US00PP29292P2

(12) United States Plant Patent
Deng

(10) Patent No.: US PP29,292 P2
(45) Date of Patent: May 15, 2018

(54) ***LANTANA CAMARA* PLANT NAMED 'UF-1013A-2A'**

(50) Latin Name: ***Lantana camara* L. (*Lantana strigocamara* R.W. Sanders).**
Varietal Denomination: UF-1013A-2A

(71) Applicant: Florida Foundation Seed Producers, Inc., Marianna, FL (US)

(72) Inventor: Zhanao Deng, Riverview, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days. days.

(21) Appl. No.: 15/530,167

(22) Filed: Dec. 8, 2016

(51) Int. Cl.
*A01H 5/00* (2018.01)

(52) U.S. Cl.
USPC ..... Plt./227

(58) Field of Classification Search
USPC ..... Plt./227
See application file for complete search history.

(56) References Cited

PUBLICATIONS

Czarnecki II, David M. et al., Ploidy Levels and Pollen Stainability of *Lantana camara* Cultivars and Breeding Lines, HortScience 49(10):1271-1276, 2014.
Czarnecki II, David Mark, Genetic Sterilization and Reproductive Biology of *Lantana camara*, A Dissertation Presented to the Graduate School of the University of Florida in Partial Fulfillment of the Requirements for the Degree of Doctor of Philosophy, University of Florida, 2011, 210 Pages.
Czarnecki II, David M. et al., UF-T3 and UF-T4: Two Sterile *Lantana camara* Cultivars, HortScience vol. 47(1):132-137, Jan. 2012.

*Primary Examiner* — Susan McCormick Ewoldt
(74) *Attorney, Agent, or Firm* — Christopher & Weisberg, P.A.

(57) ABSTRACT

A new and distinct cultivar of *Lantana camara* plant named 'UF-1013A-2A', characterized by its moderate vigor, mounding growth habit, dense branches, round plant form and canopy, free flowering, bright yellow and red flowers, little fruiting, few seeds, high level of female infertility, low level of pollen stainability, high level of male infertility, and lack of hybridization with *Lantana depressa*.

4 Drawing Sheets

ACKNOWLEDGMENT OF FEDERAL RESEARCH SUPPORT

This invention was made with government support under FLA-GCR-005065 and FLA-GCR-005507 awarded by the National Institute of Food and Agriculture, USDA. The government has certain rights in the invention.

Genus and species: *Lantana camara* L. (*Lantana strigocamara* R. W. Sanders).

Cultivar denomination: 'UF-1013A-2A'.

CROSS-REFERENCE TO RELATED APPLICATION n/a

BACKGROUND OF THE NEW CULTIVAR

The present invention relates to a new and distinct cultivar of *lantana*, botanically known as *Lantana camara*, and hereinafter referred to by the name 'UF-1013A-2A'. *Lantana camara* is a member of Verbenaceae. Plants of this species attract numerous species of butterflies, tolerate harsh environmental conditions, have low maintenance requirements, and are easy to grow. Plants of *L. camara* are highly desirable for use in containers, hanging baskets, and landscapes. Commercial production of *L. camara* is widespread in the nursery industry, especially in the southern United States. This species has escaped cultivation through fruit/seed dispersal and has hybridized (as pollen donors) with

*Lantana depressa*, a rare species native to Florida, resulting in its classification as a Category I invasive species in Florida (Florida Exotic Pest Plant Council, 2015). There has been a strong need for the development of infertile cultivars in *L. camara*.

The new *Lantana* cultivar 'UF-1013A-2A' is a product of a planned breeding program in Balm, Fla. The primary objective of the breeding program is to create new infertile *lantana* cultivars with desirable plant stature, dense branching habits, and attractive flower colors.

The new *Lantana* cultivar 'UF-1013A-2A' resulted from a planned cross between a proprietary breeding line DROP-25 and cultivar 'Landmark Flame Improved' ('Balandimfla', an abandoned U.S. Plant patent application Ser. No. 11/015,489). The stated cross was made in fall 2010 in Balm, Fla. The new *Lantana* cultivar 'UF-1013A-2A' was discovered and selected in Balm, Fla. in April 2012 as one flowering plant within the progeny of the stated cross.

Asexual propagation of the new *Lantana* cultivar 'UF-1013A-2A' by vegetative cuttings in a controlled environment in Balm, Fla. since 2012 has shown that the unique features of this new *lantana* are stable and reproduce true to type in successive generations.

Plant Breeder's Rights for this cultivar have not been applied for. The new *Lantana* cultivar 'UF-1013A-2A' has not been made publicly available more than one year prior to the filing of this application.

SUMMARY OF THE INVENTION

The new *Lantana* cultivar 'UF-1013A-2A' has not been observed under all possible environmental conditions. The phenotype of the new cultivar may vary with variations in environment and cultural practices such as temperature, light intensity, fertilization, irrigation, and application of plant growth regulators without any change in genotype.

The following traits have been repeatedly observed and are determined to be the unique characteristics of the new *Lantana* cultivar. These characteristics in combination distinguish 'UF-1013A-2A' as a new and distinct cultivar of *Lantana:*

1. moderate plant vigor;
2. mounding and upwardly spreading growth habit;
3. dense branching;
4. round plant form and canopy;
5. free flowering;
6. yellow and red-colored flowers;
7. production of attractive plants in containers;
8. little fruiting and no or few berries, little seed production, and high level of female fertility;
9. low pollen stainability; and
10. no to little hybridization potential with *Lantana depressa.*

Plants of the new *Lantana* cultivar 'UF-1013A-2A' differ from plants of the female parent in the following characteristics:

1. plants of 'UF-1013A-2A' are triploids, while plants of DROP-25 are tetraploids;
2. plants of 'UF-1013A-2A' are mounding and have dense branches, while plants of DROP-25 have fewer branches and an erratic branching habit;
3. plants of 'UF-1013A-2A' are more vigorous and taller;
4. plants of 'UF-1013A-2A' produce no or few fruit, no or few seeds, and are highly female-infertile, while plants of DROP-25 are more female-fertile and produce more fruit; and
5. plants of 'UF-1013A-2A' have low pollen stainability or viability, while plants of DROP-25 have higher pollen stainability or viability.

Plants of the new *Lantana* cultivar 'UF-1013A-2A' differ from plants of the male parent, 'Landmark Flame Improved', in the following characteristics:

1. plants of 'UF-1013A-2A' are triploids, while plants of 'Landmark Flame Improved' are diploids;
2. plants of 'UF-1013A-2A' are mounding and have a round form and canopy, while plants of 'Landmark Flame Improved' are much larger, spreading, and have an open canopy;
3. flowers of 'UF-1013A-2A' are yellow-colored when initially open and turn red when matured, while flowers of 'Landmark Flame Improved' are gold to orange;
4. plants of 'UF-1013A-2A' produce no or few fruit or seeds and are highly female-infertile, while plants of 'Landmark Flame Improved' are female-fertile and produce more fruit and seeds; and
5. plants of 'UF-1013A-2A' have low pollen stainability or viability, while plants of 'Landmark Flame Improved' have higher pollen stainability or viability.

Plants of the new *Lantana* cultivar 'UF-1013A-2A' can be compared to 'Bandana® Red' ('Bant Reda09', U.S. Plant Pat. No. 20,531). In side-by-side comparisons conducted in Balm, Fla., plants of the new *Lantana* cultivar 'UF-1013A-2A' differed from plants of 'Bandana® Red' in the following characteristics:

1. plants of 'UF-1013A-2A' have a more upright growth habit;
2. plants of 'UF-1013A-2A' have a denser canopy;
3. the leaf apex of plants of 'UF-1013A-2A' is more pointed with smaller serrations, while the leaf apex of plants of 'Bandana® Red' is more rounded with wider serrations; and
4. mature flowers of 'UF-1013A-2A' are redder than the mature flowers of 'Bandana® Red'.

Plants of the new *Lantana* cultivar 'UF-1013A-2A' can be compared to 'Lucky™ Flame Improved' ('Balucraim', commercial cultivar not patented). In side-by-side comparisons conducted in Balm, Fla., plants of the new *Lantana* cultivar differed from plants of 'Lucky™ Fame Improved' in the following characteristics:

1. plants of 'UF-1013A-2A' were more upright and have a fuller canopy, while plants of 'Lucky™ Flame Improved' have a more open canopy;
2. inflorescences of 'UF-1013A-2A' are larger than those of 'Lucky™ Flame Improved';
3. mature flowers of 'UF-1013A-2A' are red, while the mature flowers of 'Lucky™ Flame Improved' are orange; and
4. flower buds of 'UF-1013A-2A' are red, while flower buds of 'Lucky™ Flame Improved' are orange in color.

DESCRIPTION OF THE FIGURES

The accompanying photographs (as shown in FIGS. 1-4) illustrate the overall appearance of the new *Lantana* cultivar 'UF-1013A-2A'. These photographs show the colors as true as can be reasonably obtained in colored reproductions of this type. Colors in the photographs may differ slightly from the color values cited in the detailed botanical description, which accurately describe the colors of the new *Lantana* cultivar.

DETAILED BOTANICAL DESCRIPTION OF THE CULTIVAR

Figure 1:
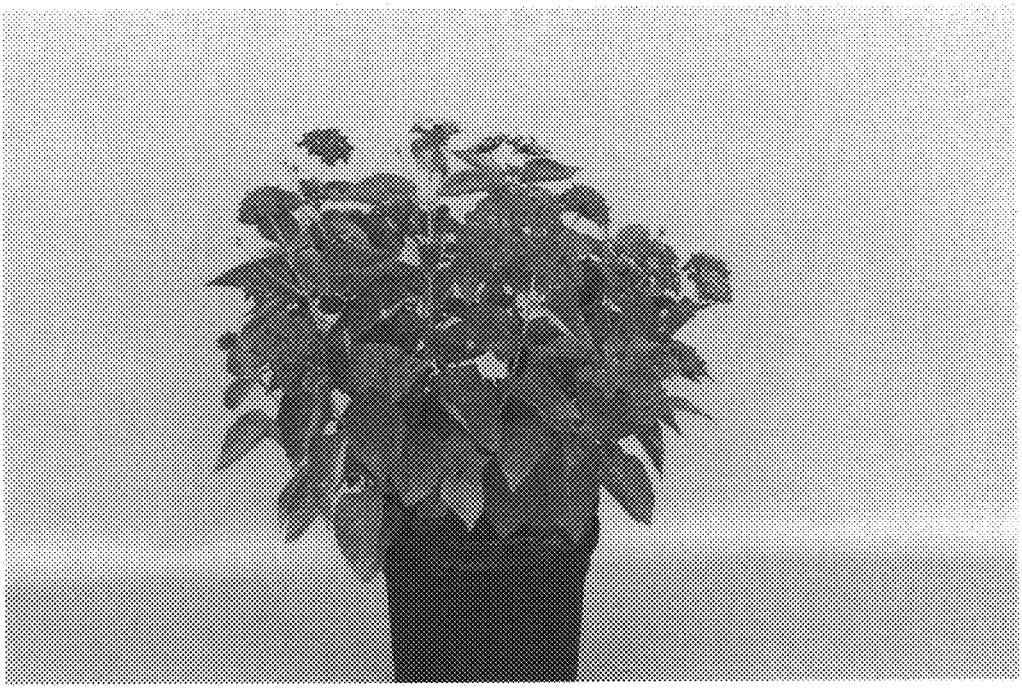
FIG. 1 shows a side perspective view of a typical flowering plant of the new *Lantana* cultivar 'UF-1013A-2A' to show its growth and branching habit, plant form, and flower color. The plant was grown in a gallon (16.5 cm in diameter and 16 cm tall) container and is shown at 16 weeks old. The plant was propagated from cuttings and sprayed once with two growth retardants.
Figure 2:
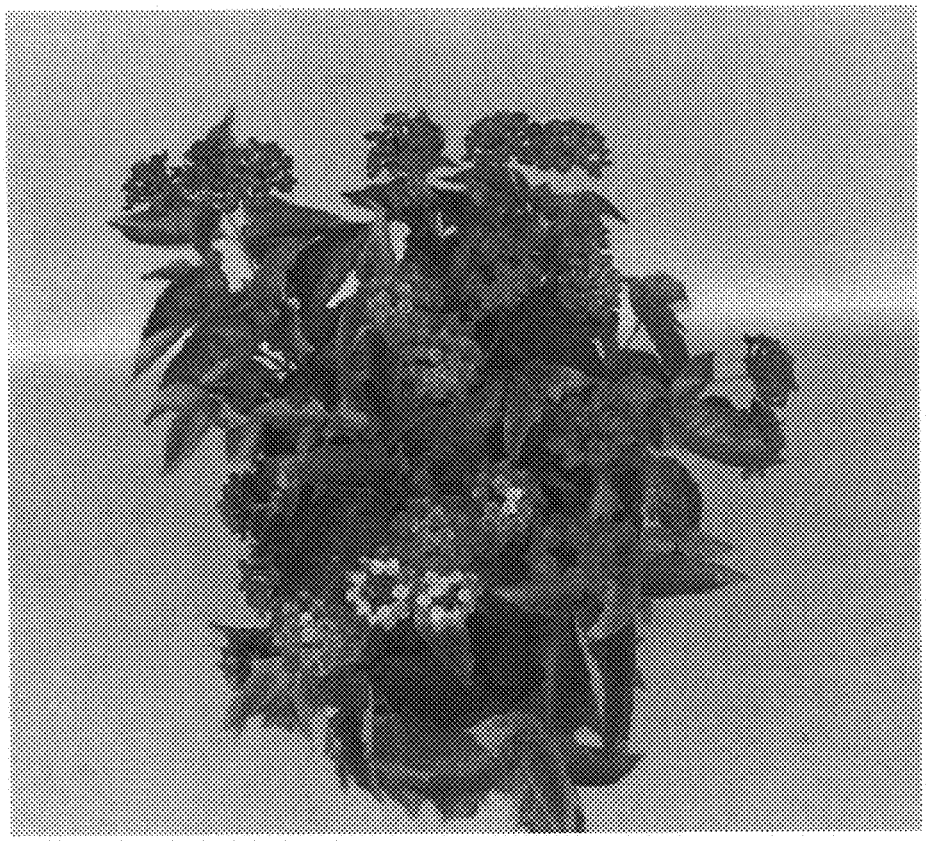
FIG. 2 shows a top view of a typical flowering plant of the new *Lantana* cultivar 'UF-1013A-2A' to show its growth and branching habit, plant form, and flower color. The plant was grown in a gallon (16.5 cm in diameter and 16 cm tall) container and is shown at 16 weeks old. The plant was propagated from cuttings and sprayed once with two growth retardants.
Figure 3:
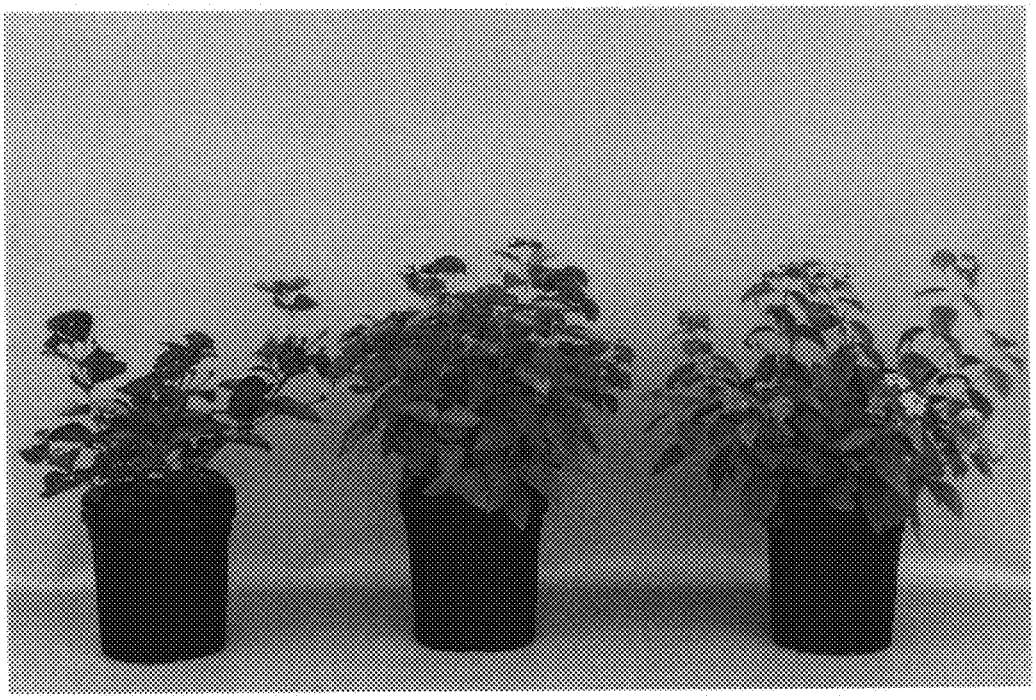
FIG. 3 shows a side perspective view of breeding line DROP-25 (left), the new *Lantana* cultivar 'UF-1013A-2A' (middle), and commercial cultivar 'Lucky™ Flame Improved' (right) when they were grown in gallon containers and at 16 weeks old. The plants were propagated from cuttings and sprayed once with two growth retardants.
Figure 4:
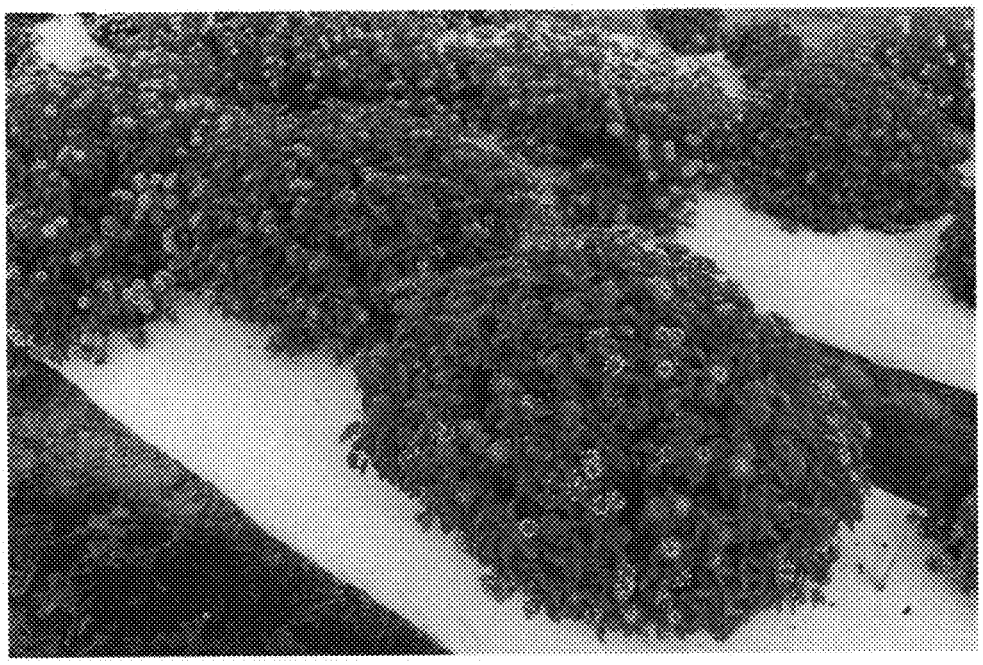
FIG. 4 shows a top view of two flowering plants of the new *Lantana* cultivar 'UF-1013A-2A' grown in a ground bed in full sun in Balm, Fla. The plants were propagated by cuttings, container-grown in a soilless mix for 95 days, transplanted to the ground bed in the week of Jun. 12, 2015, and grown in the ground for 124 days. The photo was taken in Balm, Fla. on Oct. 14, 2015.

In the following description, color references are made to The Royal Horticultural Society (R.H.S.) Colour Chart, 1986 Edition, except where general terms of ordinary dictionary significance are used.

DESCRIPTION OF GROWING CONDITIONS

Plants of the new *Lantana* cultivar 'UF-1013A-2A' used for the description were grown in the summer of 2016 in Balm, Fla. for 11 weeks from when terminal cuttings were made. Plants were planted in a 10.2-cm container and pinched at four weeks and sprayed once with growth retardants at six weeks. Plants were grown outdoors for three weeks in early September in Balm, Fla. before flower color descriptions were made. During the production of the plants in a polypropylene-covered shadehouse, temperatures ranged from about 22.2° C. to about 35.5° C.

BOTANICAL DESCRIPTION

Botanical classification:

*Family*.—Verbenaceae.

*Botanical name*.—*Lantana camara* L. (*Lantana strigocamara* R. W. Sanders).

*Common name*.—*Lantana*.

*Cultivar*.—'UF-1013A-2A'.

Parentage:

*Female or seed parent*.—Plant from breeding line DROP-25.

*Male or pollen parent*.—'Landmark Flame Improved'.

Propagation:

*Type*.—Terminal cutting.

*Time to initiate roots, summer*.—Approximately ten days at 27° C.

*Time to initiate roots, winter*.—Approximately ten days at 27° C.

*Time to develop roots, summer*.—Approximately 21 days at 27° C.

*Time to develop roots, winter*.—Approximately 21 days at 27° C.

Root description: Fine, fibrous.

*Color*.—Close to white (RHS 155B) initially, greyed-yellow (RHS 161C) with development and with streaks of greyed-brown (RHS 199C).

*Rooting habit*.—Freely branching.

Plant description:

*Type*.—Flowering subshrub.

*Plant form*.—Upright and outwardly upright plant habit.

*Growth habit*.—Uniformly mounded plant form and canopy; dense branching; two lateral branches potentially forming at every node; pinching enhances lateral branch development.

*Plant height*.—Approximately 27.5 cm.

*Plant diameter*.—Approximately 31.5 cm×28 cm.

*Lateral branches*.—Length: Approximately 20 cm. Diameter: Approximately 2.8 mm. Internode length: Approximately 2.4 cm. Strength: Strong, but flexible. Texture: Rough, pubescent. Color, young: Close to yellow-green (RHS 144C). Color, woody: Close to greyed-brown (RHS 199D).

*Stem*.—Quantity of main branches per plant: Approximately five to six. Quantity of leaves per branch: Approximately 13-15. Length of stem: Approximately 15-23 cm. Diameter: Approximately 5.4 mm. Length of internodes: Approximately 1.5-3 cm. Texture: Pilose and having a few glandular hairs. Color: Close to greyed-brown (RHS 199D) with streaks close to greyed-brown (RHS 199A) and brown (RHS 200D).

Foliage description:

*Arrangement*.—Opposite; simple.

*Length*.—Approximately 6.5-8.5 cm.

*Width*.—Approximately 4.6-5.7 cm.

*Shape*.—Ovate. Apex: Acute. Base: Obtuse with truncate tendencies.

*Margin*.—Serrate.

*Teeth along margins per leaf*.—Approximately 34-44.

*Texture, upper and lower surfaces*.—Leathery, rough, coarse; pubescent.

*Luster*.—Upper surface: Slightly glossy. Lower surface: Dull.

*Color, developing and fully expanded foliage*.—Upper surface, developing: Close to green (RHS 137B). Upper surface, expanded: Close to green (RHS 137A). Lower surface, developing: Close to green (RHS 137D). Lower surface, expanded: Close to green (RHS 137C).

*Venation pattern*.—Pinnate, arcuate.

*Color of veins*.—Upper surface: Close to green (RHS 137A). Blends in with the leaf color. Lower surface: Close to yellow-green (RHS 145C) for the midrib; primary veins are close to yellow-green (RHS 148B).

*Petiole*.—Length: Approximately 1.5-2.5 cm. Diameter: Approximately 2.2 mm. Texture, both surfaces: Slightly pubescent. Color: Upper surface: Close to yellow-green (RHS 144B). Lower surface: Close to yellow-green (RHS 144D).

Inflorescence description:

*Flower type*.—Small salverform flowers arranged in axillary umbels. Flowers face mostly upward or outward.

*Flowering habit*.—Very freely flowering, with potentially two inflorescences per node. Typically about 28-30 flowers per umbel, flowering continuous and consistent, spring until late frost in the autumn. Flowers are self-cleaning.

*Flowering longevity on the plant*.—Approximately one week.

*Fragrance*.—Faint, pleasant.

*Inflorescence diameter*.—Approximately 4 cm.

*Inflorescence height*.—Approximately 2 cm.

*Number of flowers per inflorescence*.—Approximately 28-30.

*Quantity of inflorescences per plant*.—Approximately 13-14.

*Flower appearance*.—Flared trumpet, corolla fused, four-parted. Flowers are circular or slightly oval in shape.

*Flower diameter*.—Approximately 1 cm×1 cm.

*Flower buds* (*before showing color*).—Length: Approximately 4.7 mm. Diameter: Approximately 5.4 mm (width). Shape: Roughly spherical to ovoid. Color: Close to yellow-green (RHS 144B).

*Bract*.—Length: Approximately 5 mm. Diameter: Approximately 1 mm. Color: Close to yellow-green (RHS 144C) with yellow-green (RHS 144A) at the apex. Texture: Outer surface: Hirsute. Inner surface: Glandular hairs on the inner surface.

*Corolla*.—Arrangement/appearance: Single whorl of four petals, fused into flared trumpet. Tube length: Approximately 1.1 cm. Throat and tube texture: Outer surface: Pubescent/slightly hirsute basally. Inner surface: Papillose. Tube color (mature): Outer surface: Close to red-purple (RHS 59B). Inner surface: Throat, close to yellow-orange (RHS 18A).

*Petal*.—Length from throat: Upper and lower petals: Approximately 5.6 mm. Lateral petals: Approximately 4.5 mm. Width: Upper and lower petals: Approximately 7 mm. Lateral petals: Approximately 5.5 mm. Shape: Spatulate to somewhat orbicular. Apex: Rounded. Margin: Entire. Degree of lobation: Slightly overlapping lobes. Petal lobe texture, upper and lower surfaces: Smooth, velvety. Color: Petal lobes, when opening (immature): Upper surface: Close to yellow (RHS 9A) that changes to close to orange-red (RHS 32A). Eye color: Close to yellow-orange (RHS 17A). Lower surface: Close to yellow (RHS 9C) and other surfaces close to red (RHS 39A). Petal lobes, fully opened (mature): Upper surface: Close to red (RHS 45B). Eye color: No eye color. Lower surface: Close to red (RHS 39B) with a small interior section of yellow (RHS 11C). Throat: Close to yellow-orange (RHS 18A). Tube: Close to red-purple (RHS 59B).

*Calyx*.—Number of sepals: One sepal per flower. Length: Approximately 5 mm. Width: Approximately 1 mm. Shape: Lanceolate. Apex: Acute. Base: Truncate. Texture: Upper surface: Pubescent. Lower surface (inside): Pubescent. Color: Apex: Close to yellow-green (RHS 144A). Base: Close to yellow-green (RHS 144C).

*Peduncles*.—Length: Approximately 4.5-6.0 cm. Diameter: Approximately 1.5 mm. Angle: Approximately 45° from the stem. Strength: Flexible, but strong. Texture: Pubescent. Color: Close to yellow-green (RHS 144A).

*Pedicels*.—Not observed, flowers not stalked.

*Stamens*.—Quantity/arrangement: Four per flower, adnate to floral tube. Length of filament: Approximately 4.5 mm. Color of filament: Close to yellow-white (RHS 158A).

*Anther*.—Shape: Oblong. Length: Approximately 1 mm. Color close to yellow (RHS 9A).

*Pistils*.—Quantity: One per flower. Length: Approximately 3 mm. Stigma shape: Oblong. Color: Close to yellow-green (RHS 144C).

*Ovary color*.—Close to yellow-green (RHS 144A).

*Pollen*.—Amount: Rarely observed.

*Fruit*.—Amount: Rarely observed.

COMPARISON WITH KNOWN CULTIVARS

Assessment of Female Fertility

Table 1 shows fruit production, seed viability, seed germination, and female fertility of the new *Lantana* cultivar 'UF-1013A-2A' and two check cultivars in two replicated field trials in Florida. The two check cultivars are 'UF-T3' (U.S. Plant Pat. No. 24,057) and 'Pink Caprice' (commercial cultivar, not patented).

Plants in the two field trials were grown outdoors in ground beds in full sun at two sites in Florida: one in Balm (southwest Florida, USDA hardiness zone 9A and AHS heat zone 10) and the other in Ft. Pierce (southeast Florida, USDA hardiness zone 9B and AHS heat zone 9-10). The experimental design used in Balm was randomized complete block with three blocks and two plants per plot. The experimental design used in Ft. Pierce was also a randomized complete block, but with four blocks and a single plant per plot. 'Pink Caprice' is very prolific in fruit (and seed) production (Czarnecki, 2011; Czarnecki et al., 2012), while 'UF-T3' is highly infertile (Czarnecki et al., 2012).

Fruit production data were collected from the field-grown plants in Balm and Ft. Pierce. The four harvests in Balm were made on August 17, September 14, October 16, and Nov. 18, 2015, respectively. The four harvests in Ft. Pierce were done on August 12, September 10, October 14, and Nov. 11, 2015, respectively. In each round of fruit harvesting, 20 peduncles were randomly sampled from each plant in the replicated field trials. Thus, approximately 120 peduncles were sampled for each cultivar grown in Balm and 80 peduncles were sampled for each cultivar grown in Ft. Pierce. Drupes on all harvested peduncles were counted, regardless of maturity. An analysis of variance and separation of mean fruit production values was conducted using JMP Pro 10.0.2 to compare the fruit production of the new *Lantana* cultivar 'UF-1013A-2A' with that of 'UF-T3' and 'Pink Caprice'. Mean values with the same letter within columns in Table 1 are not significantly different by the Fisher's Least Significant Difference (LSD) procedure at $P<0.05$.

As shown in Table 1, 'Pink Caprice' produced the largest number of drupes among all the entries in the two replicated trials. Each peduncle bore an average of 7.941 drupes in Ft. Pierce and 10.313 drupes in Balm, with an overall average of 9.127 across the two sites and four harvests. The number of drupes 'UF-T3' produced per peduncle ranged from 0 to 0.100 and averaged to 0.043 across two experimental sites and over 4 months. The number of drupes per peduncle for the new *Lantana* cultivar 'UF-1013A-2A' ranged from 0 to 0.050 and averaged to 0.015 across the two sites over the 4 months. This level of fruit production in 'UF-1013A-2A' represents greater than 99% reduction from the fruit production of 'Pink Caprice'.

Seeds were extracted from mature drupes collected from the above experiments. Seeds were cleaned, air-dried, and germinated. Due to having few seeds in 'UF-1013A-2A' and 'UF-T3', seeds from four harvests at each site were combined before germination. Seeds of 'Pink Caprice' were sent to a commercial seed testing laboratory (Midwest Seed Services, Brookings, S. Dak.) for seed viability tests. The new *Lantana* cultivar 'UF-1013A-2A' and 'UF-T3' produced few or no seeds at either site and were therefore not tested for viability.

As shown in Table 1, seeds of 'Pink Caprice' showed an average of 65.0% viability, germinated readily, with an average germination percentage of 45.0% in 60 days. For 'UF-T3', a total of seven and two seeds were collected from Balm and Ft. Pierce trials, respectively. One of the nine seeds germinated, resulting in an 11.1% germination. Plants of the new *Lantana* cultivar 'UF-1013A-2A' at both Balm and Ft. Pierce site did not produce any mature seeds over four months. Therefore, no seed germination data were available for 'UF-1013A-2A'.

Fruit (seed) production per peduncle and seed germination are the primary factors determining *lantana*'s female fertility. These two characteristics are factored into a female fertility index (FFI) by multiplying fruit production per peduncle and seed germination. The FFI for 'Pink Caprice' and 'UF-T3' was 4.107, and 0.005, respectively. Because of the lack of seed germination data, it was not possible to calculate the FFI for the new cultivar. However, based on its triploidy and extremely low fruit production, it was expected that the FFI for the new cultivar would be similar to that of 'UF-T3' and close to zero.

TABLE 1

| Lantana cultivar | Peduncles examined (no.) | | Fruit per peduncle (no.) | | |
|---|---|---|---|---|---|
| | Balm | Ft. Pierce | Balm | Ft. Pierce | Average |
| 'UF-1013A-2A' | 481 | 320 | 0.023 b | 0 b | 0.012 |
| 'UF-T3' | 480 | 320 | 0.046 b | 0.041 b | 0.044 |
| 'Pink Caprice' | 480 | 320 | 10.313 a | 7.941 a | 9.127 |

| Lantana cultivar | Seed viability (%) | Seeds planted (no.) | Seed germination (%) | Female fertility (FFI) |
|---|---|---|---|---|
| 'UF-1013A-2A' | — | — | — | — |
| 'UF-T3' | — | 9 | 11.1 | 0.005 |
| 'Pink Caprice' | 65.0 | 100 | 45.0 | 4.107 |

Assessment of Pollen Stainability

Table 2 shows pollen stainability of the new *Lantana* cultivar 'UF-1013A-2A' and two check cultivars ('UF-T3' and 'Pink Caprice') when their plants were grown in Balm and Ft. Pierce, Fla. in full sun in 2015. Two pollen staining experiments were conducted. In Experiment 1, newly opened flowers were collected from *Lantana* plants grown in Balm, Fla. in late July 2015, and anthers were extracted from the flowers and collected into a 1.5-mL Eppendorf tube. The collected anthers were stained with $10^{-6}$ M fluorescein diacetate (FDA) (Sigma-Aldrich, St. Louis, Mo.) in 0.22 M sucrose at room temperature in the dark for 1 hour (Czarnecki et al., 2014). Stained anthers were transferred onto a microscope slide and covered with a coverslip. Pollen grains in the anthers were released by gently tapping and pressing the coverslip and then examined under a fluorescent microscope. Plump, round pollen grains fluorescing bright yellowish green light were considered stainable, while misshaped, non-fluorescing, or unevenly, lightly fluorescing pollen grains were counted as non-stainable. In Experiment 2, flowers were collected from *Lantana* plants grown in Ft. Pierce, Fla. in mid-August 2015. Anther staining and pollen examination were performed as described in Experiment 1.

Pollen stainability data (in percentage) were arcsine-transformed before analysis of variance was performed. Means with the same letter within the column of Table 2 are not significantly different by the LSD procedure at $P<0.05$. The analysis of variance and mean separation were conducted using the software JMP Pro 12.0.1.

As shown in Table 2, the average pollen stainability of the new *Lantana* cultivar 'UF-1013A-2A' was 3.0%, comparable to the average pollen stainability of cultivar 'UF-T3'. The average pollen stainability of 'Pink Caprice' was 73.1%, similar to previous results (Czarnecki et al., 2014). The pollen stainability (or male fertility) of the new *Lantana* cultivar 'UF-1013A-2A' was reduced substantially (95.9%) from that of 'Pink Caprice'.

TABLE 2

| Cultivar | Pollen grains examined (no.) | | Pollen stainability (%) | | |
|---|---|---|---|---|---|
| | Experiment 1 | Experiment 2 | Experiment 1 | Experiment 2 | Average |
| 'UF-1013A-2A' | 2275 | 1759 | 2.2 c | 3.7 b | 3.0 |
| 'UF-T3' | 2760 | 1752 | 5.3 b | 4.9 b | 5.1 |
| 'Pink Caprice' | 1094 | 1271 | 70.8 a | 75.3 a | 73.1 |

Assessment of Hybridization Potential with *Lantana Depressa*

Table 3 shows the hybridization potential of the new *Lantana* cultivar 'UF-1013A-2A' with *L. depressa* as compared to 'UF-T3' and 'Pink Caprice'.

Hand pollination experiments were performed in a greenhouse in Balm, Fla. in June and July 2015 to assess the hybridization potential of the new *Lantana* cultivar 'UF-1013A-2A', as a male or female parent, with *L. depressa*. 'UF-T3' and 'Pink Caprice' were included in the hand pollination experiments as an infertile and a fertile check, respectively. Stock plants of all *Lantana* cultivars and *L. depressa* were grown in 1-gallon plastic containers and arranged into three blocks. The experimental unit was two containerized plants. Temperatures inside the greenhouse ranged from 21° C. to 33° C. No supplemental lighting was provided. Plants were drip-irrigated twice a day. Fresh anthers were collected from mature unopened flowers of male parents and applied immediately to emasculated flowers of female parents. At maturity, fruit produced by the pollinated flowers were collected and counted, and seeds were extracted and germinated to determine seed germination percentages.

Fruit set data (in percentage) were arcsine-transformed before analysis of variance was performed in JMP Pro 12.0.1. Means with the same letter within the column are not significantly different by the LSD procedure at $P<0.05$.

As shown in Table 3, 'Pink Caprice', as a male parent, caused an average of 8.6% fruit set on *L. depressa*. When pollinated with *L. depressa*, 'Pink Caprice' flowers showed 19.7% fruit set. Seeds from crosses between 'Pink Caprice' and *L. depressa* or vice versa showed 11.1% or 19.7% seedling emergence. 'UF-T3' caused 0.3% fruit set on *L. depressa* flowers and showed 0.8% fruit set after being pollinated with *L. depressa*. None of the seeds emerged as seedlings.

As a male parent, the new *Lantana* cultivar 'UF-1013A-2A' did not cause any fruit set on *L. depressa* flowers, nor did it set any fruit after having been hand-pollinated with *L. depressa*. Thus, the new cultivar did not hybridize with *L. depressa* when they were used as a male or a female parent in hand pollinations. These data also confirm the high level of male and female infertility in 'UF-1013A-2A'.

TABLE 3

| Cultivar | Flowers pollinated (no.) | Fruit set (%) | Seedling emergence (%) |
|---|---|---|---|
| | *L. depressa* as the female parent | | |
| 'UF-1013A-2A' | 353 | 0 b | — |
| 'UF-T3' | 368 | 0.3 b | 0 |
| 'Pink Caprice' | 388 | 8.6 a | 11.1 |

TABLE 3-continued

| Cultivar | Flowers pollinated (no.) | Fruit set (%) | Seedling emergence (%) |
|---|---|---|---|
| | *L. depressa* as the male parent | | |
| 'UF-1013A-2A' | 558 | 0 b | — |
| 'UF-T3' | 467 | 0.8 b | |
| 'Pink Caprice' | 452 | 19.7 a | 15.8 |

I claim:

1. A new and distinct *Lantana* plant named 'UF-1013A-2A' as illustrated and described herein.

* * * * *